United States Patent [19]

Fröhlen et al.

[11] Patent Number: 5,608,099

[45] Date of Patent: Mar. 4, 1997

[54] PROCESS FOR THE RECOVERY OF TRIBUTYL PHOSPHATE FROM SPENT HYDRAULIC OILS

[75] Inventors: Hans-Günter Fröhlen; Hans-Dieter Block; Wolfgang Ohlendorf; Hans-Heinrich Moretto; Peter Schmidt, all of Leverkusen, Germany

[73] Assignee: Bayer Aktiengesellschaft, Leverkusen, Germany

[21] Appl. No.: 548,795

[22] Filed: Nov. 1, 1995

[30] Foreign Application Priority Data

Nov. 8, 1994 [DE] Germany .................... 44 39 820.4

[51] Int. Cl.⁶ .................................................. C07F 9/02
[52] U.S. Cl. ................................................... 558/150
[58] Field of Search .................................... 558/150

[56] References Cited

U.S. PATENT DOCUMENTS

| | | | |
|---|---|---|---|
| 3,708,508 | 1/1973 | Schulz | 252/364 |
| 3,996,341 | 12/1976 | Lee | 423/589 |
| 4,205,023 | 5/1980 | Anzenberger, Sr. | 260/990 |
| 4,227,972 | 10/1980 | Hernandez et al. | 203/37 |
| 4,264,534 | 4/1981 | Anzenberger, Sr. | 260/990 |
| 4,620,024 | 10/1986 | Davis et al. | 558/113 |
| 4,741,857 | 5/1988 | Horwitz et al. | 252/184 |
| 5,082,602 | 1/1992 | Uetake et al. | 252/627 |
| 5,258,539 | 11/1993 | Okazaki | 558/150 |

*Primary Examiner*—Johann Richter
*Assistant Examiner*—Laura R. Cross
*Attorney, Agent, or Firm*—Sprung Horn Kramer & Woods

[57] ABSTRACT

A process for the recovery by distillation of tributyl phosphate (TBPO) from spent hydraulic oils, which are employed particularly in aircraft used for civilian air traffic.

2 Claims, No Drawings

PROCESS FOR THE RECOVERY OF TRIBUTYL PHOSPHATE FROM SPENT HYDRAULIC OILS

The present invention relates to a process for the recovery by distillation of tributyl phosphate (TBPO) from spent hydraulic oils, which are employed particularly in aircraft used for civilian air traffic.

Common hydraulic oils for use in aircraft for civilian air traffic are, for example, the oils having the trade names Hyjet® IV and Skydrol® Ld 4. These oils are miscible with one another in any proportion and can accordingly also be used as mixtures. The content of tributyl phosphate in these oils is approximately 80% by weight in the case of Hyjet® IV and approximately 50% by weight in the case of Skydrol® Ld 4. The content of tributyl phosphate in the spent oils or mixtures thereof is as a rule between 50 and 80% by weight.

The spent hydraulic oils based on tributyl phosphate have hitherto been disposed of in suitable combustion plants. Recovery of the tributyl phosphate constituent from these spent oils has not as yet been carried out owing to the complicated composition, although it would be desirable both on ecological and on economic grounds.

The object of the present invention is, therefore, to provide a process which permits the economic recovery of the tributyl phosphate constituent from the spent hydraulic oils, and consequently to reduce to a minimum the residual portion to be disposed of, in particular the portion to be burnt.

This object is fulfilled by the process according to the invention.

The invention provides a process for the recovery of tributyl phosphate from spent hydraulic oils, which is characterized in that, after separating off the water present in the spent hydraulic oils, the tributyl phosphate is separated off from the remaining constituents of the oil in one or more steps by distillation at a reduced pressure of less than or equal to ($\leq$) 100 mbar, preferably of $\leq$15 mbar, in the final step and at a temperature in the distillation receiver of $\leq$230° C., preferably $\leq$200° C.; the distillate, consisting mainly of tributyl phosphate, is collected by cooling to temperatures of below 50° C., to this distillate is added a solution of sodium butoxide in butanol in a quantity such that the acidic constituents are trapped in the distillate, optionally tempering is conducted for 30 minutes to 90 minutes at temperatures of up 100° C., the distillate thus treated is again subjected to distillation at a pressure of $\leq$5 mbar and at a temperature of $\leq$160° C., this second distillate is freed from butanol and the tributyl phosphate remaining as residue is purified by distillation.

First the entire tributyl phosphate is roughly separated from the remaining constituents of the oil in one step or in several partial steps by distillation at a reduced pressure of not more than 100 mbar, preferably of not more than 15 mbar, in the final partial step and at temperatures at the bottom of the column of up to 230° C., preferably of up to 200° C., after removal of the water. A distillate consisting mainly of tributyl phosphate is collected by cooling to temperatures of below about 50° C. The acidic portions, in particular phenolic portions such as, for example, 2,6-di-tert.-butyl cresol, are neutralized with sodium butoxide. The crude tributyl phosphate pretreated in this manner is then rectified to form a highly pure product.

The invention is explained in more detail by means of the following examples.

EXAMPLE 1

A sample of a spent, yellowish-brown colored hydraulic oil obtained from an aircraft on investigation was found to have the following values:

Density (20° C.): 1.018 g/cm$^3$

Refractive index (20° C.): 1.4487

Viscosity (20° C.): 14.7 mPa.s

Acid number: 0.42 mg KOH/g

Water content: 4.0% by weight 1660 g of the above-mentioned hydraulic oil was fractionally distilled, initially at 100 mbar and subsequently at 2 mbar, in a distillation apparatus equipped with a 2 l three-necked flask containing a stirrer and a thermometer and a packed column (600×45 mm) filled with saddles 6×6 mm in size. The temperature at the bottom of the column was initially 65° C. and subsequently 200° C. The reflux ratio was 1:1.

The composition of the individual fractions was determined by means of gas chromatography.

| Fraction | Temperature at head [°C] | Temperature at base [°C] | Pressure [mbar] | Weighed sample [g] | Water | Phenol [%] | TBPO [%] | Di-tert.-butyl cresol [%] | Dibutyl phenyl phosphate [%] |
|---|---|---|---|---|---|---|---|---|---|
| First runnings (two-phase) | to 122 | 65–154 | 100 | 62 | approx. 64.5 | approx. 0.9 | approx. 11.6 | approx. 0.5 | — |
| Main fraction | 122–123 | 154–200 | 2 | 871 | — | approx. 0.5 | approx. 97.6 | approx. 1.0 | approx. 0.5 |

In a dry ice cold trap connected in tandem 34 g of material was found which, according to gas chromatography, consisted to the extent of 76.5% of water and contained in addition 1.8% of phenol, 0.3% of TBPO and 0.2% of di-tert. butyl cresol.

The constituents of the dark-colored, low-viscosity distillation residue, which was obtained in a quantity of 689 g, were determined by means of mass spectrometry and P$^{31}$ nuclear magnetic resonance spectroscopy. In particular the following compounds were found in the following quantities by weight:

Tributyl phosphate: 0.8%

Dibutylphenyl phosphate: 34.8%

Butyldiphenyl phosphate: 10.9%

Dibutylisopropylphenyl phosphate: 14.3%

Butyldi(isopropylphenyl) phosphate: 14.5%

Higher-boiling phosphorus-free components: approx. 25%

240 g of a 6.5% by weight butanolic sodium butoxide solution was added to the tributyl phosphate thus obtained (organic phase of the first runnings and main fraction) and the reaction mixture was tempered at 100° C. for 1 hour with stirring.

In order to separate them from newly formed non-volatile components, all volatile components were distilled off via a bridge at a pressure of 2 mbar and a maximum temperature at the bottom of the column of 148° C. 35 g remained as residue. The contents of the dry ice cold trap (68 g) were combined with the distillate (980 g). After the butanol had been distilled off at a pressure of 100 mbar and at a temperature at the bottom of the column of up to 120° C., the tributyl phosphate was distilled over, with a high degree of purity, at between 1.5 and 2 mbar through a bubble-tray column having 8 trays. Initially 42 g of first runnings distilled over at a reflux ratio of 5:1. The main fraction was then distilled off without reflux. The quantity of the main fraction was 822 g. The main fraction showed a tributyl phosphate concentration of 99.5%.

EXAMPLE 2

(Procedure not according to the invention)

In this attempt to obtain pure tributyl phosphate in one step from the material by multiple-stage distillation, as in Example 1, on distilling the identical quantity of hydraulic oil using the same vacuum-producing device through a column having 18 trays at a reflux ratio of 3:1, only a tributyl phosphate contaminated with decomposition products, substantially phenol, was obtained as the condensable phase at the top of the column. The attempt to isolate pure tributyl phosphate did not succeed.

EXAMPLE 3

The first step, involving the rough separation of tributyl phosphate by distillation, is carried out as in Example 1. 18.8 ml of a 25% by weight solution of sodium methoxide is then added and distillation carried out in order to separate off non-volatile constituents. The fine distillation is carried out through a bubble-tray column having 8 trays. The product does not meet the requirements and has a content of 9.3% of methyldibutyl phosphate.

With a corresponding addition of 3.5 g of sodium hydroxide instead of sodium methoxide, a complete elimination of the phenols from the product after the fine distillation is not achieved either.

As employed herein "trapping" of the acidic constituents means converting them to non-volatile form.

It will be understood that the specification and examples are illustrative but not limitative of the present invention and that other embodiments with the spirit and scope of the invention will suggest themselves to those skilled in the art.

We claim:

1. A process for the recovery of tributyl phosphate from a spent hydraulic oil, comprising separating off the water present in the spent hydraulic oil, separating off the tributyl phosphate from the remaining constituents of the oil by distillation at a reduced pressure of 100 mbar to produce a first distillate principally comprising tributyl phosphate and at a temperature in the distillation receiver of about $\leq 230°$ C., collecting the first distillate by cooling to below about 50° C., adding to this first distillate a solution of sodium butoxide in butanol in a quantity such that the acidic constituents are trapped in the distillate, optionally tempering for about 30 minutes to 90 minutes at a temperature up to about 100° C., subjecting the first distillate to a second distillation at a pressure of about $\leq 5$ mbar and at a temperature of about 160° C., in the second distillation removing butanol and then distilling off purified tributyl phosphate.

2. The process according to claim 1, wherein in the first distillation the temperature in the distillate receiver is about $\leq 200°$ C.

* * * * *